United States Patent [19]

Ono et al.

[11] 4,321,410
[45] Mar. 23, 1982

[54] METHOD OF STRIPPING UNREACTED MATERIALS IN UREA SYNTHESIS PROCESS

[75] Inventors: Hiroshi Ono, Fujisawa; Hidetsugu Fujii, Mobara; Haruyuki Morikawa, Funabashi; Akito Fukui, Inba, all of Japan

[73] Assignees: Mitsui Toatsu Chemicals, Inc.; Toyo Engineering Corporation, both of Tokyo, Japan

[21] Appl. No.: 240,170

[22] Filed: Mar. 3, 1981

[30] Foreign Application Priority Data

Mar. 13, 1980 [JP] Japan ................. 55-030893

[51] Int. Cl.$^3$ ........................... C07C 126/02
[52] U.S. Cl. ......................... 564/67; 564/70
[58] Field of Search ............... 564/67, 70, 73

[56] References Cited

U.S. PATENT DOCUMENTS

| 3,347,915 | 10/1967 | Fauser | 564/67 |
| 3,725,210 | 4/1973 | Otsuka et al. | 564/67 X |
| 3,952,055 | 4/1976 | Mavrovic | 564/67 |
| 4,086,271 | 4/1978 | Mavrovic | 564/67 |
| 4,088,685 | 5/1978 | Mavrovic | 564/67 |
| 4,256,662 | 3/1981 | Gorlovsky et al. | 564/67 |

FOREIGN PATENT DOCUMENTS

| 112968 | 12/1964 | Czechoslovakia | 564/70 |
| 46-11009 | 3/1971 | Japan | 564/67 |

Primary Examiner—John Doll
Attorney, Agent, or Firm—Fisher, Christen & Sabol

[57] ABSTRACT

In a process in which a urea synthesis effluent obtained by reacting ammonia with carbon dioxide is subjected to a stripping step of bringing the urea synthesis effluent into countercurrent contact with carbon dioxide under heating to obtain an aqueous urea solution containing a small amount of ammonia and ammonium carbamate, the improvement comprises first bringing the urea synthesis effluent is into contact with a separated gas evolved in the stripping step under adiabatic conditions or with a little cooling. The use of the above process enables a reduction in size of the stripper and a recovery of the high pressure steam without keeping the ammonia to carbon dioxide molar ratio lower than that of the conventional method.

6 Claims, 3 Drawing Figures

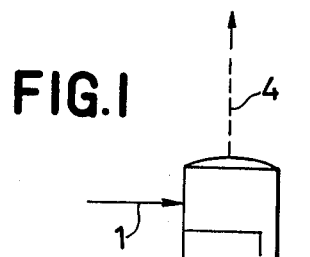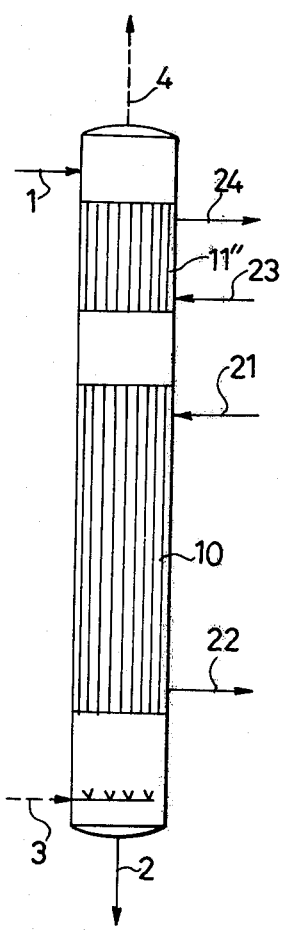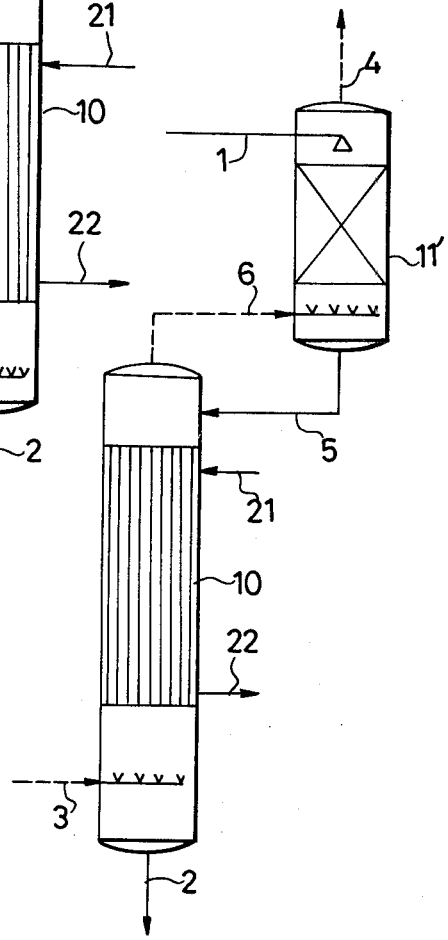

METHOD OF STRIPPING UNREACTED MATERIALS IN UREA SYNTHESIS PROCESS

BACKGROUND OF THE INVENTION (1) Field of the Invention

This invention relates to a method of stripping unreacted materials from a urea synthesis effluent intermediately obtained in a urea synthesis process from ammonia and carbon dioxide. More particularly, it relates to a method of stripping unreacted materials in a urea synthesis process which comprises first bringing a urea synthesis effluent intermediately obtained from ammonia and carbon dioxide into contact with a gas containing carbon dioxide under adiabatic conditions or with a little cooling, followed by the conventional carbon dioxide stripping process.

(2) Description of the Prior Art

The urea synthesis reaction from ammonia and carbon dioxide is normally effected under the conditions of a temperature of from 170° to 210° C., a pressure of from 130 to 300 kg/cm² (gauge pressure, and so forth) and an ammonia to carbon dioxide molar ratio of from 2.5 to 6.0, whereby from 40 to 80% of the carbon dioxide is converted to urea and the balance remains in the form of ammonium carbamate. The excess ammonia and ammonium carbamate contained in a resulting urea synthesis composition consisting of urea, water, excess ammonia and ammonium carbamate (hereinafter referred to as a urea synthesis effluent) are first separated as ammonia gas and carbon dioxide gas and a small amount of residual ammonia and ammonium carbamate contained in the aqueous urea solution are also separated in a subsequent step.

Ammonia and carbon dioxide thus separated are recovered in a gaseous state, or in the form of a condensate or of a solution thereof absorbed in water, a dilute aqueous ammonium carbonate solution, an aqueous urea solution, or the like to be recycled to the urea synthesis.

Several processes for separating excess ammonia and ammonium carbamate from a urea synthesis effluent as ammonia gas and carbon dioxide gas for purpose of recovery are known in the art. The so-called carbon dioxide stripping process, in which the urea synthesis effluent is brought into countercurrent contact with carbon dioxide gas under heating, is known as one of the typical examples of the conventional processes known in the art.

In accordance with the carbon dioxide stripping process, the excess ammonia and ammonium carbamate can be separated in a gaseous state at such a temperature as not to be extremely high even under relatively high pressure, for example, the urea synthesis pressure, so that the recovered ammonia and carbon dioxide can be recycled directly to the urea synthesis in the gaseous state. In addition to easiness of the recycle operation of the separated gas, heat recovery can be effected under the urea synthesis pressure which makes the temperature level advantageous. On the other hand, the separated gas can also be recycled to the urea synthesis either after condensing it or after absorbing it in a solvent such as water, a dilute aqueous ammonium carbonate solution, or an aqueous urea solution. Absorption under relatively high pressure such as the above requires a lesser amount of the solvent when the absorption is effected at an identical temperature, or requires about the same amount of the solvent even when the absorption is effected at a little higher temperature compared with the absorption in the separating operation under relatively lower pressure so as to be advantageous to both recycle operation and heat economy even though either absorption temperature may be chosen as above.

However, in the carbon dioxide stripping process, an intimate correlation between the stripping step and the composition of the urea synthesis effluent to be stripped, may make this process ineffective, depending on the composition of the urea synthesis effluent.

For example, when the ammonia concentration in the urea synthesis effluent to be stripped is too high, the contact of the urea synthesis effluent with carbon dioxide under heating first results in the absorption of carbon dioxide in the urea synthesis effluent instead of the decomposition of ammonium carbamate. Of course, the stripping is effected by bringing the urea synthesis effluent into countercurrent contact with carbon dioxide, and as the stripping operation proceeds, the amount of carbon dioxide absorbed in the urea synthesis effluent is gradually decreased to such an extent that the decomposition of ammonium carbamate finally proceeds. However, the decomposition step takes a considerably longer period of time to be completed, resulting in the necessity of enlarging the stripper and consequently, in operational and economical disadvantages.

In order to overcome the above problem, it is necessary to employ a urea synthesis effluent having a low concentration of ammonia, that is, a urea synthesis effluent obtained by a urea synthesis under the condition of a low ammonia to carbon dioxide molar ratio.

However, in the urea synthesis reaction represented by the following equation:

$$2NH_3 + CO_2 \rightleftharpoons NH_2CONH_2 + H_2O$$

as an excess amount of ammonia is increased, the conversion of carbon dioxide to urea is increased, and conversely as the excess amount of ammonia is decreased, the conversion of carbon dioxide to urea is decreased. Accordingly, the decrease in the ammonia to carbon dioxide molar ratio decreases the conversion of carbon dioxide to urea and increases the amount of by-product ammonium carbamate based on the amount of urea obtained, resulting in increasing the load of the stripper for the decomposition of ammonium carbamate and in increasing the amount of heat required therefor. Although the heat used for the decomposition of ammonium carbamate is mostly recoverable as low pressure steam, the fact is that more valuable high pressure steam used in the stripper is recovered only as less valuable low pressure steam, resulting in being economically disadvantageous.

SUMMARY OF THE INVENTION

An object of the present invention is to provide an operationally and economically advantageous method of stripping unreacted materials from a urea synthesis effluent, using a stripper as small as possible.

Another object of the present invention is to provide a heat-saving method of stripping unreacted materials from a urea synthesis effluent without lowering the ammonia to carbon dioxide molar ratio in the urea synthesis reaction.

In order to attain the above objects, this invention provides a method of stripping unreacted materials in the urea synthesis process which comprises first bringing the urea synthesis effluent into contact with the separated gas withdrawn from the above-noted step under adiabatic conditions or with a little cooling, prior to the conventional stripping step wherein unreacted materials in the urea synthesis effluent are stripped by countercurrent contact with carbon dioxide under heating.

BRIEF DESCRIPTION OF THE DRAWINGS

FIG. 1 shows a stripping column comprising an upper contact portion consisting of a plate tower and a lower falling-film stripping portion.

FIG. 2 shows a stripping column comprising an upper contact portion consisting of a packed bed and a lower falling-film stripping portion.

FIG. 3 shows a stripping column comprising an upper contact portion consisting of a wetted-wall column and a lower falling-film stripping portion.

DETAILED DESCRIPTION OF PREFERRED EMBODIMENTS

When a urea synthesis effluent obtained by the urea synthesis reaction at a high ammonia to carbon dioxide molar ratio and consequently, having a high content of ammonia is subjected directly to the carbon dioxide stripping, the problems as described above arise. However, it has been found that the contact of the urea synthesis effluent with a carbon dioxide containing gas results in a partial absorption of carbon dioxide in the urea synthesis effluent and a concurrent evaporation of ammonia in an amount corresponding approximately to the amount of absorption heat thereof, and thereafter, the urea synthesis effluent can be subjected directly to the carbon dioxide stripping with the same result as in the case of a urea synthesis effluent having a low content of ammonia. The rate of the absorption of carbon dioxide and that of the concurrent evaporation of ammonia are so high with little or no temperature change that there is little or no difference between the amount of heat required for the separation of excess ammonia and the decomposition of ammonium carbamate and that required in the case where the urea synthesis effluent is separated by heating instead of subjecting it to the stripping process. Thus, a urea synthesis effluent obtained at a high ammonia to carbon dioxide molar ratio and consequently, containing a large excess of ammonia can also be subjected to carbon dioxide stripping without any disadvantages in heat economy.

That is, the present invention provides a method of stripping unreacted materials which comprises first bringing a urea synthesis effluent into countercurrent contact with a separated gas obtained in a stripping step under adiabatic conditions or with a little cooling, prior to the stripping step in which the urea synthesis effluent obtained by reacting ammonia with carbon dioxide under predetermined conditions is brought into countercurrent contact with carbon dioxide under heating to strip the majority of excess ammonia and ammonium carbamate and to obtain the aqueous urea solution containing a small amount of ammonia and ammonium carbamate and the separated gas consisting of ammonia, carbon dioxide and water.

The conditions required for the practice of the method of the present invention will be described below. The urea synthesis temperature is not particularly specified, but normally ranges from 170° to 210° C. as the conventional urea synthesis temperature range, preferably from 180° to 200° C. When the urea synthesis temperature is lower than 170° C., the reaction rate is markedly lowered and a urea synthesis autoclave having a large capacity becomes necessary. On the other hand, when above 210° C., the equilibrium pressure of the urea synthesis effluent is increased to such an extent that a urea synthesis autoclave having a larger pressure resistance becomes necessary. The water to carbon dioxide molar ratio is not specifically limited, but is normally in the range of from 0.2 to 1.5, preferably from 0.3 to 1.0. The molar ratio less than 0.2 makes difficult the recycle operation of the recovered unreacted materials to urea synthesis. On the other hand, the molar ratio above 1.5 makes the conversion of carbon dioxide to urea in the urea synthesis reaction much lower.

The ammonia to carbon dioxide molar ratio as a urea synthesis condition is preferably in the range of from 3.0 to 6.0, more preferably from 3.5 to 4.5 and in the above molar ratio range, the amount of the urea synthesis effluent based on the amount of urea thus obtained is minimized. When the molar ratio is less than 3.0, the conversion of carbon dioxide to urea is decreased and the amount of steam required for stripping unreacted carbon dioxide is increased. When the molar ratio is above 6.0, the ammonia content in the urea synthesis effluent is excessively increased and increases the amount of steam required for stripping as well.

In the practice of the present invention, the urea synthesis pressure, the pressure under which stripping is effected and the pressure under which the separated gas is brought into contact with the urea synthesis effluent in the stripping step, are particularly important. The urea synthesis pressure is determined depending on the temperature, the ammonia to carbon dioxide molar ratio and other conditions, but it corresponds principally to the same pressure as that which the urea synthesis composition exhibits at the equilibrium thereof or a little higher. The urea synthesis pressure in the present invention is preferably in the range of from 140 to 250 kg/cm$^2$, more preferably from 150 to 200 kg/cm$^2$.

The pressure under which stripping is effected is required to be such a pressure as to make it possible to recycle the total amount of the gas separated by stripping to the urea synthesis step without using a large amount of an absorbent such as water, a dilute aqueous ammonium carbonate solution, or an aqueous urea solution. The above pressure may be normally in the range of from 15 to 250 kg/cm$^2$; nevertheless, it is practically most preferable to be the same pressure as the urea synthesis pressure because of the advantages for the recycle operation of the gas separated by stripping into urea synthesis and for the recovery of the heat generated in the condensation of the separated gas or in the absorption thereof in water, a dilute aqueous ammonium carbonate solution or an aqueous urea solution.

The pressure under which the separated gas is brought into contact with the urea synthesis effluent may be selected between the urea synthesis pressure and the pressure under which stripping is effected, but is preferred to be the same pressure as the pressure under which stripping is effected in order to eliminate the pressurization of the gas separated by stripping. When the urea synthesis pressure and the pressure under which stripping is effected are identical, the pressure under which the separated gas is brought into contact with the urea synthesis effluent is set to be identical therewith.

The contact of the separated gas with the urea synthesis effluent may be effected by use of any conventional gas-liquid contacting means such as a bubble tower, a plate tower, a packed bed, a wetted-wall column, a spray tower, a means of making both gas and liquid pass through the same piping or a means of making both gas and liquid pass through the same piping fitted with baffle plates for promoting mixing of gas with liquid therein. However, the plate tower, packed bed and wetted-wall column are usually used in order to make the efficiency of the countercurrent contact between the separated gas and urea synthesis effluent high. Further, it is operationally and economically advantageous to fit these columns for bringing the separated gas into contact with the urea synthesis effluent prior to the stripping step in a single unit together with the stripper, so that both steps may be effected therein.

Another important condition in the step of bringing the separated gas into contact with the urea synthesis effluent is to effect this step under adiabatic conditions or with a little cooling in order to increase the rate of absorption of carbon dioxide into the urea synthesis effluent and concurrently, the rate of evaporation of ammonia, whereby the rate of dissolution of carbon dioxide is increased to shorten the required contact time of the separated gas with the urea synthesis effluent, and the hydrolysis of urea to ammonium carbamate and the formation of biuret as a by-product can be suppressed.

As described above, the present invention provides a method of stripping the unreacted materials in the urea synthesis effluent which comprises first bringing the carbon dioxide containing gas separated in a stripping step into contact with the excess ammonia containing urea synthesis effluent produced under the condition of a high ammonia to carbon dioxide molar ratio and an adiabatic condition or a little cooling, prior to subjecting the urea synthesis effluent to the carbon dioxide stripping step which is effected countercurrently under heating.

In the method of the present invention, the urea synthesis is carried out under the condition of a high ammonia to carbon dioxide molar ratio and therefore, the conversion of carbon dioxide to urea is increased and the amount of by-product ammonium carbamate based on the amount of urea thus formed is decreased, resulting in a decrease in the load for the decomposition thereof in the stripping step and consequently, in a saving in the consumption of heat therefor. Further, the step in which the carbon dioxide containing gas separated in the stripping step is brought into contact with the urea synthesis effluent is one of the features of the present invention, and since the absorption of carbon dioxide and the evaporation of ammonia are performed concurrently and rapidly therein, the resulting urea synthesis effluent can readily be subjected to stripping with carbon dioxide under heating, resulting in shortening of the time required in the stripping step, in reduction of the apparatus size, and in saving of heat required.

Thus, the method of the present invention has remarkable effects in comparison with the conventional carbon dioxide stripping process, such as being capable of attaining reduction in size of the apparatus, saving of heat required and improvements in operational stability, as well as capable of making it easy to recover the secondarily produced heat.

Specific embodiments of the present invention will be particularly described with reference to FIG. 1, FIG. 2 and FIG. 3.

FIG. 1 shows a stripping column comprising an upper contact portion 11 consisting of a plate tower and a lower falling-film stripping portion 10. The urea synthesis effluent is introduced into the contact portion 11 from line 1 and flows down through the plate tower to enter the stripping portion 10, while the ammonia contained therein is stripped out with the separated gas and rises upward. Thereafter, the urea synthesis effluent reaches the bottom of the stripping column, while the major part of the ammonium carbamate contained in the urea synthesis effluent being decomposed to evolve ammonia and carbon dioxide to be sent to the succeeding step via line 2. On the one hand, carbon dioxide is introduced to the stripping portion 10 through line 3, and at the same time a high pressure steam for heating is introduced from line 21 and the resulting condensate is withdrawn from line 22. On the other hand, ammonia and carbon dioxide, separated in the stripping portion 10, rise through the contact portion 11 and pass to the succeeding step via line 4.

FIG. 2 shows an apparatus comprising a contact portion 11' consisting of a packed bed in place of the contact portion 11 consisting of the plate tower in FIG. 1 and the contact portion 11' and the stripping portion 10 are separately arranged from each other so as to form respective columns. The urea synthesis effluent is introduced into the contact portion 11' from line 1, flows down through the packed bed to reach the bottom of the column, while evolving ammonia contained therein on contact with the separated gas rising upward via line 6 from the stripping portion 10 and enters the stripping portion 10 via line 5. Thereafter, the same procedure as mentioned in FIG. 1 is repeated.

FIG. 3 shows such an apparatus that the contact portion 11 consisting of the plate tower in FIG. 1 is replaced by a contact portion 11" consisting of a wetted-wall column. The same procedures as in the apparatus shown in FIG. 1 are repeated except that the contact portion 11" is cooled by passing a coolant from line 23 to line 24.

The present invention will be particularly illustrated in the following Example, it being, however, understood that the example should not be construed as limiting the invention.

EXAMPLE

A urea synthesis reaction is effected under the conditions of a pressure of 175 kg/cm$^2$, a temperature of 195° C., an $NH_3$ to $CO_2$ molar ratio of 3.9 and a $H_2O$ to $CO_2$ molar ratio of 0.51 to obtain 171.4 t/day of a urea synthesis effluent consisting of 60 t/day of urea, 61.0 t/day of $NH_3$, 19.2 t/day of $CO_2$, and 31.2 t/day of $H_2O$.

The urea synthesis effluent is sent to a stripper having a contact portion consisting of a plate tower and a falling-film stripping portion as shown in FIG. 1 and operated under a pressure substantially equal to the urea synthesis pressure and on the other hand, 44 t/day of $CO_2$ is introduced from below the stripping portion. As the result, the urea synthesis effluent is brought into adiabatic and countercurrent contact with 97.0 t/day of the separated gas resulting from the stripping portion and consisting of 28.4 t/day of $NH_3$, 62.3 t/day of $CO_2$ and 6.3 t/day of $H_2O$ to evolve ammonia while absorbing carbon dioxide, and is converted to 156 t/day of a liquid consisting of 60.0 t/day of urea, 39.9 t/day of $NH_3$, 25.8 t/day of $CO_2$ and 30.3 t/day of $H_2O$ to flow into the stripping portion. Thus, 103.0 t/day of a urea solution at 190° C. consisting of 60.0 t/day of urea, 11.5 t/day of $NH_3$, 7.5 t/day of $CO_2$ and 24.0 t/day of $H_2O$ is obtained from the bottom of the stripping portion, and on the other hand, 112.4 t/day of gas consisting of 49.5 t/day of $NH_3$, 55.7 t/day of $CO_2$ and 7.2 t/day of $H_2O$ is withdrawn from the top of the contact portion.

The above recovered gas is absorbed in a recovered solution resulting from the absorption in water of ammonia and carbon dioxide obtained by the vacuum distillation of the urea solution withdrawn from the bottom of the stripping portion and consisting of 46.0% of $NH_3$, of $CO_2$ and 24% of $H_2O$, and then it is recycled to urea synthesis along with 34 t/day of make-up liquid ammonia. In accordance with the material balance as above, the continuous operation of the urea synthesis process is carried out.

The consumption of the steam of 25 kg/cm² in the stripping portion of this Example is 0.72 t per 1 t of the obtained urea.

The material balance of this Example is illustrated in the following Table.

COMPARATIVE EXAMPLE

A urea synthesis reaction is effected under the same conditions as in Example except for using an $NH_3$ to $CO_2$ molar ratio of 2.8, and a $H_2O$ to $CO_2$ molar ratio of 0.50, to obtain 170.6 t/day of a urea synthesis effluent consisting of 60.0 t/day of urea, 46.7 t/day of $NH_3$, 30.6 t/day of $CO_2$ and 33.3 t/day of water.

The urea synthesis effluent is passed through the falling-film stripping portion excluding the contact portion of the apparatus in FIG. 1 under the same conditions as in the Example to obtain 105.7 t/day of a urea solution at 190° C. consisting of 60.0 t/day of urea, 11.3 t/day of $NH_3$, 7.6 t/day of $CO_2$ and 26.8 t/day of $H_2O$ from the bottom of the stripping portion, and on the other hand, 108.9 t/day of gas consisting of 35.4 t/day of $NH_3$, 67.0 t/day of $CO_2$ and 6.5 t/day of $H_2O$ is withdrawn from the top of the stripping portion.

The consumption of the steam of 25 kg/cm² in the stripping portion of the Comparative Example is 0.90 t per 1 t of the obtained urea. The comparison of the steam unit as above with the steam unit of 0.72 t of the Example shows that the consumption of steam is 20% less by the method of the present invention compared with the conventional method.

The material balance for Comparative Example is illustrated in the following Table.

TABLE

| | | Example | | Comparative Example |
|---|---|---|---|---|
| Urea Synthesis Conditions | Pressure | 175 kg/cm² | Pressure | 175 kg/cm² |
| | Temperature | 195° C. | Temperature | 195° C. |
| | $NH_3/CO_2$ molar ratio | 3.9 | $NH_3/CO_2$ molar ratio | 2.8 |
| | $H_2O/CO_2$ molar ratio | 0.51 | $H_2O/CO_2$ molar ratio | 0.50 |
| Urea Synthesis Effluent (t/day) | Urea | 60.0 | Urea | 60.0 |
| | $NH_3$ | 61.0 | $NH_3$ | 46.7 |
| | $CO_2$ | 19.2 | $CO_2$ | 30.6 |
| | $H_2O$ | 31.2 | $H_2O$ | 33.3 |
| | Total | 171.4 | Total | 170.6 |
| Urea Solution at Outlet of Contact Portion (t/day) | Urea | 60.0 | | |
| | $NH_3$ | 39.9 | | |
| | $CO_2$ | 25.8 | | |
| | $H_2O$ | 30.3 | | |
| | Total | 156.0 | | |
| Urea Solution Withdrawn from Stripper (t/day) | Urea | 60.0 | Urea | 60.0 |
| | $NH_3$ | 11.5 | $NH_3$ | 11.3 |
| | $CO_2$ | 7.5 | $CO_2$ | 7.6 |
| | $H_2O$ | 24.0 | $H_2O$ | 26.8 |
| | Total | 103.0 | Total | 105.7 |
| Gas Withdrawn from Stripper (t/day) | $NH_3$ | 49.5 | $NH_3$ | 35.4 |
| | $CO_2$ | 55.7 | $CO_2$ | 67.0 |
| | $H_2O$ | 7.2 | $H_2O$ | 6.5 |
| | Total | 112.4 | Total | 108.9 |
| Amount of Recycle to Urea Synthesis (t/day) | $NH_3$ | 61.0 | $NH_3$ | 46.7 |
| | $CO_2$ | 63.2 | $CO_2$ | 74.6 |
| | $H_2O$ | 13.2 | $H_2O$ | 15.3 |
| | Total | 137.4 | Total | 136.6 |
| Amount of Feed to Urea Synthesis (t/day) | $NH_3$ | 95.0 | $NH_3$ | 80.7 |
| | $CO_2$ | 63.2 | $CO_2$ | 74.6 |
| | $H_2O$ | 13.2 | $H_2O$ | 15.3 |
| | Total | 171.4 | Total | 170.6 |
| Urea Solution after Vacuum Distillation (t/day) | Urea | 60.0 | Urea | 60.0 |
| | $NH_3$ | 0 | $NH_3$ | 0 |
| | $CO_2$ | 0 | $CO_2$ | 0 |
| | $H_2O$ | 18.0 | $H_2O$ | 18.0 |
| | Total | 78.0 | Total | 78.0 |

What is claimed is:

1. In a method of stripping unreacted materials in a urea synthesis process comprising subjecting a urea synthesis effluent obtained by reacting ammonia with carbon dioxide to a stripping step in which the urea synthesis effluent is brought into countercurrent contact with carbon dioxide under heating to obtain an aqueous urea solution containing a small amount of ammonia and ammonium carbamate, the improvement comprising first bringing said urea synthesis effluent into contact with a separated gas, evolved in the stripping step, under adiabatic conditions or with cooling prior to the stripping step.

2. A method as claimed in claim 1, wherein said urea synthesis effluent is formed under an ammonia to carbon dioxide molar ratio of from 3.0 to 6.0.

3. A method as claimed in claim 1 or 2, wherein the urea synthesis process is performed under a gauge pressure ranging from 140 to 250 kg/cm², and the stripping step and contacting step of the urea synthesis effluent with said separated gas are performed under substantially the same gauge pressure ranging from 15 to 250 kg/cm².

4. A method as claimed in claim 1 or 2, wherein the urea synthesis process, the stripping step and the contacting step of the urea synthesis effluent with the separated gas are performed under a pressure substantially identical to one another.

5. A method as claimed in claim 1 or 2, wherein the contacting step of the urea synthesis effluent with the separated gas is performed countercurrently in a plate tower, a packed bed, or a wetted-wall column.

6. A method as claimed in claim 5 wherein said contacting step and said stripping step are performed in a single unit.

* * * * *